United States Patent
Leipold et al.

(10) Patent No.: US 9,102,906 B2
(45) Date of Patent: Aug. 11, 2015

(54) ADHERING ACIDIC SANITARY CLEANER AND FRAGRANCER

(75) Inventors: Joachim Leipold, Reutlingen (DE); Edgar Jaeschke, Filderstadt (DE); Matthias Fritz, Gomaringen (DE)

(73) Assignee: BUCK-CHEMIE GMBH, Herrenberg (DE)

( * ) Notice: Subject to any disclaimer, the term of this patent is extended or adjusted under 35 U.S.C. 154(b) by 0 days.

(21) Appl. No.: 13/812,813

(22) PCT Filed: Jul. 12, 2011

(86) PCT No.: PCT/EP2011/061845
§ 371 (c)(1),
(2), (4) Date: Jan. 28, 2013

(87) PCT Pub. No.: WO2012/013490
PCT Pub. Date: Feb. 2, 2012

(65) Prior Publication Data
US 2013/0130962 A1 May 23, 2013

(30) Foreign Application Priority Data
Jul. 27, 2010 (DE) .......... 10 2010 032 417

(51) Int. Cl.
C11D 17/00 (2006.01)
A01N 25/24 (2006.01)
C11D 1/34 (2006.01)
A01N 41/02 (2006.01)
A01N 57/12 (2006.01)

(52) U.S. Cl.
CPC .............. *C11D 17/00* (2013.01); *A01N 25/24* (2013.01); *A01N 41/02* (2013.01); *A01N 57/12* (2013.01); *C11D 1/345* (2013.01)

(58) Field of Classification Search
None
See application file for complete search history.

(56) References Cited

U.S. PATENT DOCUMENTS

| | | | |
|---|---|---|---|
| 3,432,494 A | 3/1969 | Chiddix et al. | |
| 3,432,495 A | 3/1969 | Chiddix et al. | |
| 3,655,569 A | 4/1972 | Hellsten et al. | |
| 4,752,411 A | 6/1988 | Melin et al. | |
| 6,524,594 B1 * | 2/2003 | Santora et al. | 424/401 |
| 6,667,286 B1 * | 12/2003 | Dettinger et al. | 510/191 |
| 2010/0158967 A1 | 6/2010 | Reid et al. | |

FOREIGN PATENT DOCUMENTS

| | | |
|---|---|---|
| DE | 19623571 A1 | 12/1997 |
| DE | 19916182 A1 | 10/2000 |
| DE | 10048887 A1 | 4/2002 |
| DE | 10356254 A1 | 10/2004 |
| DE | 102004056554 A1 | 5/2006 |
| DE | 102008051173 A1 | 4/2010 |
| EP | 1318191 A1 | 6/2003 |
| GB | 2397823 A | 8/2004 |
| WO | 97/40133 A1 | 10/1997 |
| WO | 99/66017 A1 | 12/1999 |
| WO | 2009/106220 A1 | 9/2009 |

OTHER PUBLICATIONS

PCT International Preliminary Report on Patentability for PCT/EP2011/061845 dated Jan. 29, 2013.

* cited by examiner

*Primary Examiner* — Necholus Ogden, Jr.
(74) *Attorney, Agent, or Firm* — Kriegsman & Kriegsman

(57) ABSTRACT

The invention relates to a sanitary composition for cleaning and/or disinfecting and/or for fragrance release, which composition is applicable directly to the sanitary unit, adheres there and can be rinsed off only after a relatively large number of rinse operations, and which composition comprises surfactants and at least one adhesion promoter, said adhesion promoter being an oxo acid of the following formula

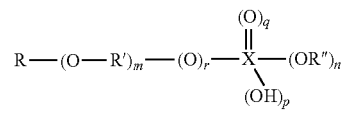

and R being an alkyl or aryl radical, R' is an alkyl or hydroxyalkyl group, R" is an alkyl, aryl or alkoxyalkyl radical, X a main group element of main groups 5 or 7 from the $3^{rd}$ period, selenium, tellurium, or a transition group element, m=1 to 50, n=0, 1, 2, q=1, 2, r=0, 1 and p=1, 2, and the viscosity of the composition, measured with a Haake viscometer, plate-cone system, PK 5 1° sensor, shear rate of 25 $s^{-1}$ and 20° C., is at least 15 000 mPas.

11 Claims, No Drawings

ADHERING ACIDIC SANITARY CLEANER AND FRAGRANCER

The invention relates to adhering sanitary cleaners and fragrancers for cleaning and/or disinfecting and/or releasing fragrance for sanitary objects such as lavatory bowls, which are also suitable for removing limescale and urine scale.

Such adhering sanitary agents are viscous, typically paste-like gels, which are applied directly to the surface of the sanitary object from a corresponding container, adhere there and can be flushed away only after a relatively large number of flushing operations. These agents are generally at least partly liquid-crystalline.

By adhering the agent to the surface of the sanitary object directly, it is not necessary to provide containers such as the so-called "WC cage" in addition, the use of which is considered by a consumer to be unhygienic, in particular when the sanitary agent is replaced and the lavatory is being cleaned.

Such adhering sanitary agents are known from WO 99/66017. As well as surfactants, water and fragrances, they also comprise adhesion promoters, for example from the category of non-ionic surfactants such as the polyalkoxyalkanes, and are viscous, solid or paste-like agents. A polarization-microscopic analysis of the cleaners known from this document shows that the cleaning agents comprise liquid-crystalline phases, in particular from hexagonal structures.

In order to prevent the surface of these adhering agents from drying out, and to provide an aesthetic and smooth surface, irrespective of the number of flushes, it is suggested in DE 100 48 887 A1 to add, additionally, an aliphatic di-, oligo- or polyhydroxy compound or ethers thereof to the agent.

A sanitary agent is known from EP 1 318 191 that comprises, as adhesion promoters, compounds from the group of block polymers comprising oligo- or polyethylene oxide and/or oligo- and/or polypropylene oxide and/or oligo- and/or polybutylene oxide, aryl ethoxylates or alkyl-aryl ethoxylates.

These known adhering sanitary agents can be applied in a simple and hygienic manner with a suitable device, adhere to the surface of the sanitary object, retain their shape and are not washed off entirely even by exposure to water, but instead only dissolve gradually after a plurality of flushes.

Furthermore, adhering sanitary agents have become known from DE 103 56 254 A1 that comprise anionic and non-ionic surfactants as adhesion promoters and silicates as thickeners.

These agents are notable for good manageability and a good cleaning effect. By the possibility of directly applying the agents, it is no longer necessary for the user to have to touch a potentially unclean toilet cage while refilling. The user can also apply the agent in an amount desired by him/her and is not limited to the pack amount provided by the manufacturer.

A further advantage of the known gelous adhering agents is that they are characterized by a clearly superior release of fragrance in comparison to molded cleaning agents.

Many of the adhering sanitary agents that have been known up until now are gelous. Due to the instability of the gel structure, however, adding otherwise typical additives for sanitary agents to these gels often leads to the destruction of the gel structure.

A further development of such adhering gels that are durable despite the addition of bleaching agents is described in DE 10 2004 056 554 A1.

A modification to the adhering agent based on further classes of specific adhesion promoters is known from WO 2009/106220 A1, with which the achievement was made for providing such an adhesive material that it can serve to affix agents in bar form to the toilet bowl, i.e. for all intents and purposes functions as an "adhesive" for rim blocks, fragrancing blocks or descaling tablets in the lavatory and still flushes away gradually.

The sanitary agents that have been known to date are neutral or alkaline and thus cannot be used in the same way as acidic cleaners for the removal of limescale and urine scale.

Adding conventional acids contained in sanitary agents, such as amidosulfonic acid, to these adhering, predominantly gelous sanitary agents, leads to the destruction of the gel structure.

Aqueous preparations for cleaning hard surfaces are known from DE 19916182 A1 to contain, among other ingredients, alkyl aryl ether phosphates. U.S. Pat. No. 4,752,411 relates to alkaline, liquid cleaning compositions which contain, among other ingredients, phosphoric acid esters. Agents for cleaning hard surfaces are known from U.S. Pat. No. 3,655,569 to contain, among other ingredients, phosphate esters. The teachings of U.S. Pat. No. 3,432,494 and U.S. Pat. No. 3,432,495 are aryl alkyl arsenic acid and the teaching of US 2010/0158967 is biocidal compositions based on selenium compounds.

The object of the present invention is to provide an adhering sanitary agent having a good cleaning capacity, by agents of which limescale and urine scale can also be effectively removed.

This object is achieved by sanitary agents comprising, as the adhesion promoter, an acidic salt of an oxo acid of the following formula:

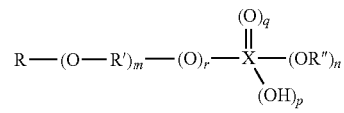

wherein R is an alkyl or aryl radical, R' is an alkyl or hydroxyalkyl group, R" is an alkyl, aryl or alkoxyalkyl radical, X is a main group element of main groups 5 or 7 from the 3rd period onward, selenium, tellurium or a transition group element, m=1 to 50, n=0, 1, 2, q=1, 2, r=0, 1 and p=1, 2, and wherein the viscosity of the agent, measured with a Haake viscometer, plate-cone system, PK 5 1° sensor, shear rate of 25 s$^{-1}$ and 20° C., is at least 15 000 mPas.

Due to the fact that the adhesion promoter of the invention is acidic, it is effective against urine scale and limescale. In addition, it shows strong adherence to hard surfaces, which can be wet or dry (ceramic, tile, metal, glass, glazed tile etc.), such that the agents comprising the adhesion promoter according to the invention also have the desired adhesion and can only be flushed away gradually after having adhered. Moreover, it has the properties of an anionic surfactant.

With the acidic adhesion promoter—different from the situation with conventional acids such as amidosulfonic acid—the gel structure in a gelous system is not destroyed.

In the field of the present invention, oxo acids are understood to be all oxygen-containing acids having an inorganic central atom.

The central atom X is an element from main group 5 or 7, or the element selenium or tellurium from main group 6, or an element from the transition group of the periodic table. It is preferable for X to be phosphorus, arsenic, antimony, selenium, tellurium, chlorine, bromine, iodine, manganese, chromium, molybdenum, tungsten, gold, and particularly preferably phosphorus, arsenic, chlorine or bromine.

The oxo acids are esterified with an organic radical having a terminal alkyl or alkyl radical R and an oligo- or polyether group. The oligo- or polyether group (OR') is an oligo- or polyalkoxy group, which can also be hydroxylated, and preferably an alkoxy or hydroxyalkoxy group with fewer than 8 carbon atoms, particularly preferably a C2 and C3, i.e. the oligoether group OR' is an ethoxy, propoxy or glyceryl group (O—C—C(H)(OH)—C—).

The terminal radical R, which is connected to the ether function, is an alkyl group or an aryl group, preferably a $C_8$-$C_{22}$ alkyl radical (branched or unbranched) and a benzyl (aryl) radical, but also a heteroaromatic.

If the free oxo acid, alongside the OH group esterified with the oligo/polyether radical and the free OH group, should have further OH groups, the further OH groups can also be esterified as long as the compound still reacts acidically.

In the variant where r=0, the alkyl radical R' is directly linked to the central atom X and thus is not bridged by a further oxygen bridge. This compound class is also possible as long as they have the necessary acidity.

The proportion of acidic adhesion promoters according to the invention in the agent should be between 1% b.w. (by weight) and 50% b.w., preferably between 3% b.w. and 30% b.w. and particularly preferably between 5% b.w. and 26% b.w.

Acidic alkyl polyglycol ether phosphates can, for example, be used as adhesion promoters according to the invention.

Particularly preferred adhesion promoters are acidic alkyl polyglycol ether phosphates, which, for example, can be obtained under the trade name Phosfetal by Zschimmer & Schwarz, Lahnstein, Germany, Crafol by the company Cognis or Naxonac by the company Nease Performance Chemicals.

These acidic, anionic surfactants are less sensitive than phosphoric acid esters to hardening components in water, such as calcium or magnesium; they possess good lime soap dispersing power; they are durable in the presence of alkalis and are compatible with anionic, amphoteric and non-ionic surfactants. Furthermore, they protect against corrosion, are completely bio-degradable and correspond to detergent regulation number 648/2004 of the European Commission.

A pH value of approximately 3.9 (0.1% solution) can be attained with a proportion of approximately 25% b.w. of the particularly preferred acidic alkyl polyglycol ether phosphates in the agent, and with a proportion of only approximately 5%, the pH value of the agent increases to 6.75 (0.1%). In order to obtain the desired lower pH value in the agent according to the invention, the proportion of acidic alkyl polyglycol ether phosphates in the agent should thus be at least 18% b.w. and preferably 25% b.w.

Alkyl polyglycol ether phosphate forms, together with water, a hard, adhesive, acidic white mass, which is sticky and flushes away gradually.

An agent comprising only alkyl polyglycol ether phosphates is acidic and shows the desired cleaning effect on limescale and urine scale; however, the surface tension and the foaming power of such an agent are low.

To improve the foaming power and to reduce the surface tension, further surfactants can be added to the agent according to the invention. In a preferred embodiment, the agent according to the invention has anionic fatty alcohol ether sulfates to improve the foaming power, which are selected, in particular, from the group of ammonium fatty alcohol ether sulfates having preferably $C_{12}$-$C_{18}$ alkyl radicals and 1 to 6 EO. A particularly preferred anionic fatty alcohol ether sulfate is triisopropanol ammonium fatty alcohol ether sulfate with 1.2 propylene glycol, which can be obtained, for example from Zschimmer & Schwarz under the trade name Zetesol TP 300.

This anionic surfactant is characterized by a very high foaming power and low surface tension; it reacts neutrally in aqueous solution; it likewise adheres well to the surface, in combination with water, and can be flushed away gradually.

The proportion of these anionic fatty alcohol ether sulfates in the agent should be up to 60% b.w., preferably between 10% b.w. and 40% b.w. and particularly preferably between 15% b.w. and 25% b.w.

In line with the present invention, it has been established that an acidic, well-adhering agent, which can be flushed away gradually only after a large number of flushing operations, is obtained on the combined use of the acidic adhesion promoter according to the invention with anionic fatty alcohol ether sulphate; the agent additionally foams and cleans well since it has low surface tension. In addition, the desired acidic pH value of the agent can be adjusted and the acidic properties of the agent can thus be adapted to the required deliming performance. A further advantage of this combination of the two surfactants is that both display the desired adhesive effect on wet and dry surfaces.

It is preferable for the ratio of the acidic alkyl polyglycol ether phosphates to anionic fatty alcohol ether sulfate to be between 1:100 and 100:1, preferably 1:10 and 10:1.

It is of course possible to add a different well-foaming and well-cleaning surfactant instead of the anionic fatty alcohol ether sulfate, such as amphoteric surfactants.

The agent according to the invention can furthermore comprise other surfactants, solvents, fragrances, colourants, disinfectants, preservatives, such as isothiazolone derivatives, or foam stabilizers such as coconut fatty acid mono/diethanolamide or alkylamine oxides, as long as the additions are stable under acidic conditions.

A further advantage of the agent according to the invention is that it possesses a high absorption capacity for perfume and can have a perfume proportion of greater than or equal to 8%. The agent typically comprises between 2% b.w. and 15% b.w. and preferably between 4% b.w. and 10% b.w. of perfume oil.

The adhesion promoters according to the invention, such as the preferred anionic alkyl polyglycol ether sulfate, form a substance similar to modelling clay when water is added, which becomes thicker the more water content there is, before reaching a maximum level of viscosity. After this maximum level has been reached, the viscosity then decreases when more water is added.

The formulations according to the invention are preferably adapted in such a way that the material has still not yet achieved its maximum viscosity level, i.e. that the material which is located on the toilet bowl, for example, becomes thicker and solidifies the first time it is subject to flushing.

The lower viscosity level of the agent, which is, where necessary, required for the application, can be set by adding polar solvents such as glycerol, alcohols such as methanol or ethanol, but also non-polar solvents such as the typical perfume solvents or even perfume oil itself. The higher the proportion of non-aqueous solvents in a material, the more liquid the agent will be.

The water concentration is generally between 20% b.w. and 80% b.w., preferably between 30% b.w. and 60% b.w. and particularly preferably between 40% b.w. and 50% b.w.

The proportion of non-aqueous solvents (including perfume oil) in the agent is generally between 0.2% b.w. and 20% b.w., preferably between 1% b.w. and 15% b.w. and particularly preferably between 2% b.w. and 14% b.w.

The surfactant:water ratio is preferably between 0.9:1 and 1.2:1 and the surfactant:total solvents ratio (including perfume oil) is preferably between 0.7:1 and 1.1:1.

In principle, all known anionic and cationic or amphoteric surfactants can be used as further surfactants.

Sulfonate and sulfate surfactants are, for example, those used as anionic surfactants. It is preferred that $C_{9-13}$ alkylbenzene sulfonates, olefin sulfonates, i.e. mixtures of alkane and hydroxyalkane sulfonates, and also disulfonates, such as are obtained, for example, from $C_{12-18}$ mono-olefins with a terminal or internal double bond using sulfonation with gaseous sulfur trioxide and subsequent alkaline or acidic hydrolysis of the sulfonation products, are considered as sulfonate-type surfactants.

Alkane sulfonates that are produced from $C_{12-18}$ alkanes, for example by sulfochlorination or sulfoxidation with subsequent hydrolysis or neutralization, respectively, are also suitable. Likewise, the esters of alpha-sulfo fatty acids (ester sulfonates) are suitable, for example the alpha-sulfonated methyl esters of hydrogenated coconut, palm kernel or tallow fatty acids.

Further suitable anionic surfactants are sulfated fatty acid glycerine esters. By fatty acid glycerol esters are meant the mono-, di- and triesters and also mixtures thereof, of the kind obtained during preparation by esterification of a monoglycerol with 1 to 3 mol of fatty acid or during the transesterification of triglycerides with 0.3 to 2 mol of glycerol. Preferred sulfated fatty acid glycerol esters are thus the sulfation products of saturated fatty acids with 6 to 22 carbon atoms, for example caproic acid, caprylic acid, capric acid, myristic acid, lauric acid, palmitic acid, stearic acid or behenic acid.

Alkali salts are preferred as alk(en)yl sulfates, in particular sodium salts of the sulfuric acid monoesters of $C_{12}$-$C_{18}$ fatty alcohols, for example from coconut fatty alcohol, tallow fatty alcohol, lauryl, myristyl, cetyl or stearyl alcohol or $C_{10}$-$C_{20}$ oxo-alcohols and those monoesters of secondary alcohols with these chain lengths. Furthermore, alk(en)yl sulfates with the specified chain length are preferred that contain a synthetic, linear alkyl radical that is produced petro-chemically, that possess the same chemical fate as the suitable compounds based on fatty chemical raw materials. 2,3-alkyl sulfates, which can be obtained as a product of Shell Oil Company under the name DAN®, are also suitable anionic surfactants.

Sulfuric acid monoesters of linear or branched $C_{7-21}$ alcohols which are ethoxylated with 1 to 6 mol of ethylene oxide, such as 2-methyl-branched $C_{9-11}$ alcohols with an average of 3.5 mol of ethylene oxide (EO), or $C_{12-18}$ fatty alcohols with 1 to 4 EO, are also suitable.

Further suitable anionic surfactants are also salts of alkylsulfosuccinic acid, which are also characterized as sulfosuccinates or sulfosuccinic acid esters, and represent the monoesters and/or diesters of sulfosuccinic acid with alcohols, preferably fatty alcohols, and particularly ethoxylated fatty alcohols. Preferred sulfosuccinates contain $C_{8-18}$ fatty alcohol radicals or mixtures thereof. Particularly preferred sulfosuccinates contain a fatty alcohol radical that is derived from ethoxylated fatty alcohols that, in themselves, are considered to be non-ionic surfactants. Here, in turn, sulfosuccinates whose fatty alcohol radicals are derived from ethoxylated fatty alcohols with a narrowed homolog distribution are particularly preferred. Likewise, it is also possible to use alk(en)yl succinic acid with preferably 8 to 18 carbon atoms in the alk(en)yl chain, or salts thereof. The anionic surfactants can be present in the form of their sodium, potassium or ammonium salts, and also as soluble salts of organic bases, such as mono-, di- or triethanolamine. It is preferable for the anionic surfactants to be present in the form of their sodium or potassium salts, in particular in the form of sodium salts.

According to the invention, it is particularly preferred for fatty alcohol ether sulfates, alkyl sulfates, alkyl benzene sulfonates and/or alkane sulfonates to be used as anionic surfactants.

As regards the optionally contained additional fragrances, these are those which are commonly known from the prior art. Mixtures of natural and synthetic odorants are to be cited as examples. Natural odorants are flower extracts (lily, lavender, rose, jasmine, neroli, ylang-ylang), stems and leaves (geranium, patchouli, petitgrain), fruits (aniseed, coriander, caraway, juniper), fruit skins (bergamot, lemon, orange), roots (mace, angelica, celery, cardamom, costus, iris, calmus), woods (pine, sandalwood, guaiacum, cedar, rosewood), herbs and grasses (tarragon, lemongrass, sage, thyme), needles and twigs (spruce, fir, pine, dwarf pine), resins and balsams (galbanum, elemi, benzoin, myrrh, frankincense, opoponax). Moreover, animal products are considered, such as civet and castoreum. Typical synthetic fragrance compounds are ester, ether, aldehyde, ketone, alcohol and hydrocarbon products. Ester fragrance compounds are, for example, benzyl acetate, phenoxyethyl isobutyrate, p-tert-butylcyclohexyl acetate, linalyl acetate, dimethyl benzyl carbinyl acetate, phenylethyl acetate, linalyl benzoate, benzyl formate, ethyl methylphenylglycinate, allyl cyclohexyl propionate, styrallyl propionate and benzyl salicylate. Benzyl ethyl ether, for example, counts as an ether; the linear alkanals with 8 to 18 carbon atoms, citral, citronellal, citronellyl oxy acetaldehyde, cyclamen aldehyde, hydroxycitronellal, lilial and bourgeonal, for example, count as aldehydes; the ionones, alpha isomethyl ionone and methyl cedryl ketone, for example, count as ketones; menthol, anethole, citronellol, eugenol, isoeugenol, geraniol, linalool, nerol, phenylethyl alcohol, tetrahydromyrcenol and terpineol count as terpene alcohols; and the terpenes and balsams belong, predominantly, to the hydrocarbons. It is preferable, however, for mixtures of various fragrances to be used, which together produce a pleasant scent.

Also, essential oils of lower volatility, which are mainly used as aromatic components, are suitable as perfume oils, for example sage oil, chamomile oil, clove oil, lemon balm oil, mint oil, cinnamon leaf oil, lime blossom oil, juniper berry oil, vetiver oil, oliban oil, galbanum oil, labolanum oil and lavender oil. It is preferable to use bergamot oil, dihydromyrcenol, lilial, lyral, citronellol, phenylethyl alcohol, alpha-hexyl cinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavender oil, muscatel, sage oil, beta-damascone, geranium oil bourbon, cyclohexyl salicylate, Vertofix Coeur, Iso E Super, Fixolide NP, evernyl, iraldein gamma, phenylacetic acid, geranyl acetate, benzyl acetate, rose oxide, romillate, irotyl and floramate, either alone or mixed together.

The dosage amount is dependent on the desired intensity of fragrance and is preferably in the range of 5% b.w. to 20% b.w., particularly preferably 6% b.w. to 8% b.w. It is particularly preferable for the fragrances to be acid-stable.

It is also possible to add olefin sulfonates, ether sulfates and/or surfactants, in particular acid methyl taurides, as foamers with a self-cleaning effect, to the agent according to the invention.

In order to prevent the agent from drying out, the agent can additionally comprise, at preferably between 5 and 15% b.w., aliphatic di-, oligo- or polyhydroxy compounds or ethers thereof, or (the) compound(s) from the group glycerol, 1,3- dihydroxypropane, 1,3- or 1,4-dihydroxybutane, 1,3-dihydroxyisobutane and/or pentaerythritol.

If desired, salts, such as sodium sulphate, can be added to the composition so as to increase the dissipation speed. The salt proportion can be up to 10% b.w., preferably up to 5% b.w.

The agent according to the invention can be applied and replaced hygienically without contact with potentially contaminated devices connected to the toilet bowl.

A fundamental advantage of the agent according to the invention is that it can be portioned according to the user's wishes. If the user desires more intensive cleaning, or if the lavatory is used frequently, it can be applied in a greater dosage accordingly.

The agent according to the invention can also be applied to different points on the sanitary object at the same time in simple fashion, for example in order to produce a consistent cleaning effect on both the right-hand and the left-hand side of a lavatory bowl.

The adhesion achieved on the sanitary object, even when applied to a vertical surface, is so good that the agent does not detach even when subjected to the additional force effect of flushed water flows.

The sanitary agent according to the invention can be flushed away only after a large number of flushing operations. The number of flushing operations is, of course, dependent on the composition of the respective sanitary agent, the amount applied and the geometry of the sanitary agent applied.

It is preferable for the agent according to the invention to be an ointment-like, paste-like, creamy or gelous material, wherein the gelous material is, in particular, liquid-crystalline and preferably has a hexagonal structure. The gels are fundamentally dimensionally stable, such that they do not "run down" or "drip".

The gels can be inserted into the lavatory bowl preferably via tubes that are comparable to toothpaste tubes, or via spraying devices or cartouches, and remain adhered there for a plurality of consecutive flushing operations.

The viscosities of these paste-like gels, which are to be determined on a Haake viscometer, plate-cone system, PK 5 1° sensor, shear rate of 25 s$^{-1}$ and 20° C., are at least 15 000 mPas. They should typically be at least 50 000 mPas, preferably at least 90 000 mPas and particularly preferably at least 110 000 mPas.

On application of a strip of 4-6 cm in length, 2 cm in breadth and 0.3-0.5 cm in thickness, the flush numbers of the agents according to the invention are between approximately 40 and 180.

The agents according to the invention are preferably transparent.

The invention is described in greater detail below by means of exemplary embodiments.

1. Production of the Agents According to the Invention

To produce the agent according to the invention, water is introduced and heated to a temperature of T>80° C. and the acidic adhesion promoter according to the invention and, if desired, further surfactant and solvent, are added and stirred. A kneadable mass is obtained. The mass "solidifies" when Phosfetal is added and it has an almost waxy consistency.

Then, after gentle cooling, the heat-sensitive perfume, which should preferably be acid-stable, is added and the surface tension and flush numbers are determined.

If desired, a colourant, for example a 1% aqueous rhodamine EB4 solution, can be added during production.

In order to increase the transparency of the agent and to avoid air bubbles being entrapped, the mass should be degassed.

The desired foam number and surface tension can be adjusted by the amount of fatty alcohol ether sulfate (such as Zetesol).

The thickening in the water/Phosfetal system first increases when water is added; the thickening exhibits a maximum level and then decreases when more water is added.

The consistency of the agent can be adjusted by adding water or other solvents, such as polar solvents (alcohols, PEG 300, PEG 400) or even perfume.

During production, the mass is adjusted in such a way that the maximum viscosity level is still not reached.

The mass thickens after production after more water has been added (continues to gel). To be able to apply the thickened mass from an applicator, the mass that is to be filled in is thinned out by a non-aqueous solvent such as alcohol or perfume (modifying agent). During the first passage of flushing over the mass in the lavatory bowl, the non-aqueous solvent is replaced successively by water. Thus the mass thickens until it has reached its maximum viscosity level.

The mass obtained can be applied by a normal applicator to a dry or damp surface, adheres there, and can be flushed away only after a large number of flushing operations.

The mass obtained thus is acidic, i.e. it removes limescale and urine scale, and it is a transparent gel.

2. Formulations According to the Invention

Various formulations of the agent produced according to the invention are compiled in Table I. This table also contains specifications as to the consistency, adhesive properties, flush number, pH value, surface tension and foam numbers of each agent.

The anionic surfactant Phosfetal 205, which can be obtained from Zschimmer & Schwarz, was used as the acidic adhesion promoter according to the invention. The pH value of a 1% solution is 2. The alkyl group is a C14-C18 group, and the "polyglycol ether" group has between 1 and 3 glycol units.

Triisopropanol ammonium fatty alcohol ether sulfate with 1,2-propylene glycol (TIPA Laureth sulfate (and) Propylene glycol) was used as the anionic fatty alcohol ether sulfate, and can be obtained from Zschimmer & Schwarz under the trade name Zetesol TP 300. The fatty alcohol radical has between 12 and 14 carbon atoms and is ethoxylated with 2.5-3 EO. The 2% aqueous solution of this surfactant reacts neutrally (pH 7).

Orange Fun, which can be obtained from the company Givaudan, was used as the perfume.

3. Determining the Foam Numbers and the Surface Tension

To determine the foam numbers, 100 ml of the parent solution, which is at 20° C., is transferred into a 250 ml volumetric flask and sealed with a PFTE stopper. Then the flask is swirled back and forth twenty times (20 times upside down). After every 30 seconds, 5 minutes and 30 minutes, we read and noted down the foam volume (ml) produced.

The determination of the surface tension was carried out using the BP2 device from the company Krüss Blasendruckmessgeräte.

TABLE I

| Test | 1 [%] | 2 [%] | 3 [%] | 4 [%] | 5 [%] | 6 [%] | 7 [%] | 8 [%] | Manufacturer |
|---|---|---|---|---|---|---|---|---|---|
| Zetesol TP 300 | 25 | 22.7 | 25 | 0 | 50 | 44.61 | 5.00 | 20 | Zschimmer & Schwarz |
| Phosfetal 205 | 25 | 22.7 | 25 | 50 | 0 | 5.71 | 44.97 | 20 | Zschimmer & Schwarz |
| Perfume (Orange Fun) | 8 | 7.27 | 5 | 5 | 5 | 4.95 | 5.06 | 20 | Givaudan |
| Water | 42 | 47.3 | 45 | 45 | 45 | 44.72 | 44.97 | 40 | De-mineralized |
| Total | 100 | 100 | 100 | 100 | 100 | 100 | 100 | 100 | |
| Consistency | Viscous/flowing | Solidified Material | Solidifies when produced | Solidifies when produced | Solidifies when produced | Solidifies when produced | Solidifies when produced | Mass too thin | |
| Flush number | ./. | Not determined | >187 | Not determined | >35 | Not determined | Not determined | ./. | |
| pH, 0.1% solution | | | 3.94 (21.3° C.) | | | 6.75; (27.3° C.) | | | |
| Adheres | No (flows) | Yes | Yes | Yes | Yes | Yes | Yes | Does not adhere | |
| Surface tension [mN/m] | | | 67.2/59.1/54.9 | 70.1; 6.3; 65.3 | 57.5; 45.9; 42.1 | 60/49.1/45/1 | | | |
| Foam [30 s, 5 min, 30 min] | | | 115/105/90 | 20; 15; 10 | 190; 170; 160 | 125/110/100 | | | |
| Total surfactant | 50 | 50 | 50 | 50 | 50 | 51.1 | 50 | 40 | |
| Surfactant:water | 1.19 | 0.96 | 1.11 | 1.11 | 1.11 | 1.13 | 1.11 | 1 | |
| Surfactant:total solvent | 1 | 0.83 | 1 | 1 | 1 | 1.01 | 1.00 | 0.67 | |

The invention claimed is:

1. Sanitary agent for cleaning and/or disinfecting and/or fragrancing, said agent being able to be applied directly to the sanitary object, adhering there and being able to be flushed away only after a large number of flushing operations, and said agent comprising surfactants and at least one adhesion promoter,
characterized in that the adhesion promoter is an oxo acid of the following formula

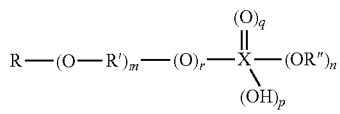

wherein R is an alkyl or aryl radical, R' is an alkyl or hydroxyalkyl group, R" is an alkyl, aryl or alkoxyalkyl radical, X is selected from the group consisting of phosphorus, arsenic, antimony, selenium, tellurium, chlorine, bromine, iodine, manganese, chromium, molybdenum, tungsten and gold, m=1 to 50, n=0, 1, 2, q=1, 2, r=0, 1 and p=1, 2, the viscosity of the agent, measured with a Haake viscometer, plate-cone system, PK 5 1° sensor, shear rate of 25 s$^{-1}$ and 20° C., is at least 15 000 mPas, the proportion of adhesion promoter in the sanitary agent is between 18% b.w. (by weight) and 50% b.w. and further characterized in that the agent comprises water in a concentration of between 20% b.w. and 80% b.w.

2. Sanitary agent according to claim 1, characterized in that the adhesion promoter is an alkyl polyglycol ether phosphate.

3. Sanitary agent according to claim 1, characterized in that it additionally comprises anionic and/or non-ionic and/or amphoteric and/or non-ionic surfactants.

4. Sanitary agent according to claim 1, characterized in that the agent comprises fatty alcohol ether sulfates.

5. Sanitary agent according to claim 4, characterized in that the proportion of fatty alcohol ether sulfates is up to 60% b.w.

6. Sanitary agent according to claim 1, characterized in that the agent comprises perfume oil.

7. Sanitary agent according to claim 1, characterized in that the flush numbers of the agent, wherein the agent is a strip of 4-6 cm in length, 2 cm in breadth and 0.3-0.5 cm in thickness applied to a lavatory bowl, are between 40 and 180.

8. Sanitary agent according to claim 1, characterized in that the agent is transparent.

9. Sanitary agent according to claim 1, characterized in that the agent is gelous.

10. Sanitary agent according to claim 1, characterized in that the proportion of the adhesion promoter in the agent is between 18% b.w. and 30% b.w.

11. Sanitary agent according to claim 6, characterized in that it comprises perfume oil in a concentration of between 2% b.w. and 15% b.w.

* * * * *